United States Patent
Egley et al.

(10) Patent No.: US 9,044,586 B2
(45) Date of Patent: Jun. 2, 2015

(54) DIALYSIS CONTROL VALVE HAVING SELF-CLEANING MODE

(71) Applicant: FRESENIUS MEDICAL CARE HOLDINGS, INC., Waltham, MA (US)

(72) Inventors: Bert D. Egley, Walnut Creek, CA (US); Philip Scott James, Pleasanton, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 92 days.

(21) Appl. No.: 13/838,701

(22) Filed: Mar. 15, 2013

(65) Prior Publication Data

US 2014/0261717 A1    Sep. 18, 2014

(51) Int. Cl.
 *F16K 31/06* (2006.01)
 *A61M 39/22* (2006.01)
 *F16K 29/00* (2006.01)

(52) U.S. Cl.
 CPC .......... *A61M 39/223* (2013.01); *F16K 31/0603* (2013.01); *F16K 29/00* (2013.01); *F16K 31/0627* (2013.01)

(58) Field of Classification Search
 CPC .. A61M 39/223; F16K 29/00; F16K 31/0627; F16K 31/0603
 USPC ............ 137/907, 625, 625.17, 625.4, 625.44, 137/15.01, 15.04–15.06, 238, 625.48; 251/129.15, 129.05
 See application file for complete search history.

(56) References Cited

U.S. PATENT DOCUMENTS

| | | | | |
|---|---|---|---|---|
| 3,215,162 A | * | 11/1965 | Carver | 137/625.44 |
| 3,379,214 A | * | 4/1968 | Weinberg | 137/625.5 |
| 3,570,807 A | * | 3/1971 | Sturman et al. | 251/65 |
| 3,598,360 A | * | 8/1971 | Merriner et al. | 251/129.15 |
| 3,919,923 A | * | 11/1975 | Haigh | 91/51 |
| 4,081,171 A | | 3/1978 | Morgan et al. | |
| 4,252,651 A | | 2/1981 | Soderstrom | |
| 4,627,461 A | | 12/1986 | Gordon | |

(Continued)

FOREIGN PATENT DOCUMENTS

WO    98-52640 A1    11/1998
WO    2013016351 A1    1/2013

OTHER PUBLICATIONS

International Search Report and Written Opinion issued in corresponding International Patent Application No. PCT/US2014/017300 dated May 20, 2014 (15 pages).

*Primary Examiner* — Kevin Lee
(74) *Attorney, Agent, or Firm* — Kilyk & Bowesox, P.L.L.C.

(57) ABSTRACT

A valve system is provided that includes an electromechanical solenoid, a gas valve including a magnetic flapper, a power source in electrical communication with the electromechanical solenoid, and a controller. The controller is configured to control the power source to supply an intermediate voltage that causes the electromechanical solenoid to move to a neutral position between a default position and a fully-actuated position. In so doing, the magnetic flapper is maintained in a neutral position between two gas ports and a flow of gas between the ports can be used to clean foreign particles from the magnetic flapper. The controller can also provide a varying voltage to the electromechanical solenoid while in the neutral position to cause vibration of the magnetic flapper and further assist in removing foreign particles. A closed loop system including a feedback circuit can be used for adjusting the voltage applied to the solenoid based on pressure sensed.

24 Claims, 7 Drawing Sheets

(56) References Cited

U.S. PATENT DOCUMENTS

| | | | |
|---|---|---|---|
| 5,113,892 A | 5/1992 | Hull et al. | |
| 5,971,889 A | 10/1999 | Ohashi et al. | |
| 6,145,806 A * | 11/2000 | Dettmann | 251/65 |
| 6,195,834 B1 | 3/2001 | Shteingold | |
| 7,782,590 B2 | 8/2010 | Bedingfield et al. | |
| 7,935,074 B2 | 5/2011 | Plahey et al. | |
| 8,609,293 B2 * | 12/2013 | Maier | 429/454 |
| 2004/0055652 A1 | 3/2004 | Erickson | |
| 2009/0213519 A1 | 8/2009 | Bedingfield | |
| 2011/0196289 A1 | 8/2011 | Plahey et al. | |
| 2013/0006171 A1 | 1/2013 | Griessmann et al. | |

* cited by examiner

DIALYSIS CONTROL VALVE HAVING SELF-CLEANING MODE

FIELD

The present invention relates to valve systems, methods of cleaning valves, and, more particularly, electromechanical flapper vales.

BACKGROUND

Many machines, including many dialysis machines, have pneumatically-controlled functions that are carried out using pneumatic valves, herein referred to as gas valves or air valves. In pneumatically-controlled dialysis machines, pressurized air can be used to control the flow of dialysate, to close safety clamps, and to carry out other important functions. Air valves that include a flapper mechanism controlled by an electromechanical solenoid are referred to as flapper valves and are used in some pneumatic dialysis machines.

To ensure patient safety, the pressures in pneumatically-controlled dialysis machines are checked often to see whether any pressure leaks have developed. Gaseous diffusion, for example, through rubber and plastic materials in a valve, can result in a constant low-level leak rate. Thus, some safety systems discriminate between such a constant leak rate and a leak rate of greater concern. An alarm system must be set at a threshold value that is just above such a constant leak rate, but even a constant leak rate can vary from valve to valve. Moreover, for any given valve, the constant leak rate can vary over time, for example, due to temperature fluctuations and altitude fluctuations.

When very small foreign particles settle between the flapper and the plastic housing of a flapper valve, small leaks can also develop. Despite using air filters to prevent foreign particles from entering a pneumatic system and its gas valves, some foreign particles nonetheless make it into the system. Particles as small as 100 microns or less, or 50 microns or less, can enter a gas valve, become stuck on the flapper, and cause a leak. The particles can also sometimes become embedded in the elastomeric material making up the flapper, especially when made of soft rubber.

Although a slightly leaking air valve resulting from foreign particle contamination may not pose a danger to a patient, if the dialysis machine cannot distinguish between such a leak and a truly dangerous leak, then the machine might shut down unnecessarily thinking the leak is more serious.

A need exists for a valve system for a pneumatically-operated dialysis machine, which can detect a valve leak caused by foreign particle contamination and automatically take action to fix it. A need also exists for a flapper valve system and method that include a self-cleaning mode to clean the valve flapper of foreign particles. A need further exists for a flapper valve system and method that can automatically detect a leak attributable to foreign particle contamination and carry out a self-cleaning mode in an attempt to clean the valve flapper.

SUMMARY

In accordance with the present invention, a valve system is provided for a pneumatically-operated dialysis machine, which can detect a valve leak caused by foreign particle contamination, and automatically take action to fix it. A flapper valve system and method are provided that include a self-cleaning mode to clean the valve flapper of foreign particles. If the self-cleaning mode is successful in fixing the leak, the dialysis machine can then resume normal operation.

According to the present invention, a valve system is provided that includes an electromechanical solenoid, a gas valve including a magnetic flapper, a power source in electrical communication with the electromechanical solenoid, and a controller. The controller is configured to control the power source to supply an intermediate voltage that causes the electromechanical solenoid to move to a neutral position between a default position and a fully-actuated position. In so doing, the magnetic flapper is maintained in a neutral position between two gas ports and a flow of gas between the ports can be used to clean debris from the magnetic flapper. The controller can also provide a varying voltage to the electromechanical solenoid while in the neutral position to cause vibration of the magnetic flapper and further assist in removing debris.

The valve system can also include a pressure sensor in operable communication with an outlet port of the gas valve, and the sensor can be configured to sense the pressure of fluid exiting or entering the outlet port. Circuitry can be included that is configured to carry a feedback signal, indicative of pressure sensed by the pressure sensor, to a controller. The controller can be configured to control the power source to increase, decrease, or maintain a voltage, based on the feedback signal, so that the pressure of fluid exiting or entering the outlet port is maintained within an acceptable range of pressures. The feedback signal can be used make sure the electromechanical solenoid maintains the flapper in the neutral position between the two gas ports.

The valve system can include an integrated circuit (IC) and a primary power supply, in electrical communication with the electromechanical solenoid. In some cases, first and second power sources can be used for providing a direct current (DC) power supply and an alternating current (AC) power supply, respectively, to the electromechanical solenoid. A switch can be provided that is in electrical communication with the IC or with the second power source, and also in electrical communication with the electromechanical solenoid. A controller can be used to actuate the switch to change between a cleaning mode position and a normal operation mode position. When the switch is switched to the cleaning mode position, the switch can cause the IC, or other circuitry, to form a different circuit for controlling the electromechanical solenoid. For example, when two power sources are used, the cleaning mode position can form a circuit that enables power supplied from a second power source to activate the electromechanical solenoid. In some cases, an AC current can thus be applied and used to vibrate the flapper while the flapper is maintained in a neutral position. The vibration can cause particles to be dislodged from the flapper. In the normal operation mode, the switch can be configured to form a different circuit through the IC, or to interrupt the electrical connection from the second power source to the electromechanical solenoid.

The present invention also provides a method of cleaning a magnetic flapper of a flapper valve in a pneumatic system, for example, in a dialysis machine. The method can include applying an activating voltage to an electromechanical solenoid of a gas valve that comprises a magnetic flapper. The activating voltage can be of sufficient strength to activate the electromechanical solenoid and move the magnetic flapper from a first position, where the magnetic flapper closes a first pneumatic port, to a neutral position where the magnetic flapper is maintained between the first pneumatic port and a second, different pneumatic port. The electromechanical solenoid can be configured such that, upon application of a second voltage that is greater than the activating voltage, the magnetic flapper is moved to a second position where it closes the second pneumatic port. The method can further entail maintaining the activating voltage so as to maintain the magnetic flapper in the neutral position between the first pneumatic port and the second pneumatic port. Gas can then be flowed around the magnetic flapper while the magnetic flapper is maintained in the neutral position. The flow of gas can come from the second pneumatic port, for example, from a pressure port, to the first pneumatic port, for example, to a vacuum port. Maintaining the flapper in the neutral position while flowing the gas can affect cleaning of the magnetic flapper, for example, by dislodging foreign particles stuck to the flapper. Applying an alternating current AC voltage or varying a DC voltage to the solenoid can further accentuate the cleaning operation by causing vibrations and/or pressure changes across the flapper.

BRIEF DESCRIPTION OF THE DRAWINGS

The accompanying drawings, which are incorporated into and constitute a part of the specification, illustrate specific embodiments of the present invention, and taken in conjunction with the detailed description of the specific embodiments, serve to explain the principles of the present invention.

DETAILED DESCRIPTION

In accordance with the present invention, a method of cleaning a gas valve is provided, and can be used to clean air valves in a pneumatically-operated dialysis machine. Although the present invention is described in great detail herein, with reference to a dialysis machine, it is to be understood that the present invention also encompasses using the systems and methods described herein for cleaning gas valves in other environments besides dialysis machines. For the sake of facilitating a thorough understanding of the present invention, however, reference is made to a pneumatically-operated dialysis machine.

In a pneumatically-operated dialysis machine, when a small leak is detected that might be attributable to foreign particle contamination of a gas valve flapper, operation of the dialysis machine can be halted and a flapper cleaning operation can be carried out. The flapper cleaning operation can be non-automated, semi-automated, or fully automated. The cleaning operation entails manipulating the flapper in an effort to dislodge or remove foreign particles that might be causing the leak detected. The cleaning operation then involves rechecking pressures to see if the leak is fixed, and if it is, normal use of the dialysis machine can be resumed.

The cleaning operation or self-cleaning mode can involve any of a variety of manipulation techniques geared at dislodging foreign particles from the gas valve flapper. In a first technique, the flapper can be toggled back-and-forth between a first position, where a first valve port is closed, and a second position, where a second valve port is closed. Toggling the flapper back-and-forth can be accomplished by intermittently applying an activating voltage to the electromechanical solenoid connected to the flapper. The activating voltage can be of sufficient strength to overcome a bias, such as a spring force, that normally maintains the flapper in a first position closing one of the valve ports. The activating voltage can be of sufficient strength to fully actuate the solenoid and move the flapper to a fully extended second position where it closes a different valve port. By removing the applied voltage, the biasing force can be of sufficient strength to move the flapper back to its original first position. After three, five, ten, twenty, or more times back-and-forth, foreign particles on the flapper can be dislodged, fixing the leak. After the cleaning operation, the valve, or pressure or vacuum from the valve, can then be checked to determine whether the procedure was successful in cleaning the flapper.

In another cleaning operation, the valve is manipulated to maintain the flapper in a neutral position for a period of time, for example, for a predetermined period of time. A voltage can be applied to the solenoid coil that would balance the forces exerted on the flapper so that the flapper can be maintained in an intermediate position between two valve ports. The voltage can be a DC voltage, an AC voltage, or a combination thereof. The forces exerted can include a biasing force, for example, as provided by a solenoid spring, along with gas pressure and vacuum forces coming from the valve ports. By positioning the flapper in the neutral position, gas would be able to move around the flapper and cause foreign particles lodged on the flapper to be blown off the flapper and removed, for example, by being sucked out of a vacuum port. The activating voltage applied to the solenoid can be varied so that the flapper moves back and forth, closer to then away from two opposing pneumatic ports. In some cases, this pulsing of the flapper toward and away from the ports can be carried out without contacting either port. A feedback signal, for example, indicative of a pressure sensed, can be used to determine whether the flapper is maintained in the neutral position during the cleaning operation. After the cleaning operation, the valve, or pressure or vacuum from the valve, can then be checked to determine whether the procedure was successful in cleaning the flapper.

In yet another cleaning operation, the valve is manipulated to maintain the flapper in a neutral position for a period of time, a first voltage is applied to the solenoid coil that balances the forces exerted on the flapper so that the flapper is maintained in an intermediate or neutral position between two valve ports. An integrated circuit can be provided such that an alternating current voltage is also applied to vibrate the flapper. The first voltage can be a DC voltage, an AC voltage, or a combination thereof. The first voltage combined with the AC voltage can result in a DC offset to an AC signal. The forces exerted can include a biasing force and gas pressure and vacuum forces coming from the valve ports. The biasing force can comprise, for example, a solenoid spring, a magnet, an iron or metal piece to which the solenoid magnet is attracted, an iron or metal piece to which the solenoid magnet is repelled, an electromagnet, or the like. By positioning the flapper in the neutral position, gas would be able to move around the flapper and cause foreign particles vibrated off of the flapper to be sucked out of the valve through a vacuum port. A feedback signal, for example, indicative of a pressure sensed, can be used to determine whether the flapper is maintained in the neutral position during the cleaning operation. After the cleaning operation, the valve, or pressure or vacuum from the valve, can then be checked to determine whether the procedure was successful in cleaning the flapper.

In any of the cleaning operations disclosed herein, a feedback circuit can be provided to control the voltage applied to the electromechanical solenoid. The feedback signal can be generated by sensing the pressure of gas entering or exiting a port to the gas valve. A pressure transducer can be used to sense the pressure at the valve port, and circuitry can be provided to generate and send a feedback signal indicative of the pressure sensed, to a controller. The controller can use the feedback signal to adjust an activating voltage that is sent to the electromechanical solenoid to control actuation of the solenoid based on the feedback signal. The activating voltage can be adjusted based on the feedback signal to maintain the magnetic flapper in the neutral position between a first pneumatic port and a second pneumatic port of the valve. For example, if the feedback signal indicates that too much pressure is exiting the valve then the activating voltage can be reduced, or increased, so that the flapper moves closer to an inlet pressure port, increasing vacuum within the valve. Likewise, if the feedback signal indicates that too little pressure is exiting the valve then the activating voltage can be increased, or reduced, so that the flapper moves closer to an inlet vacuum port, thus increasing pressure within the valve. Whether the activating voltage should be reduced or increased to move the flapper in a particular direction depends on how the valve and solenoid are configured.

The feedback signal that can be used to control the activating voltage sent to the solenoid can be generated in a very fast time. In an exemplary embodiment, the time it takes to sense the pressure, generate the feedback signal, deliver the signal to the controller, and control the power source to send an adjusted activating voltage, can be two times faster than the time it takes for the solenoid to move the flapper from a first position where it closes a first port, to a second position where it closes a second port. Circuitry can be used that can evaluate a signal, indicative of pressure sensed, at a fast enough rate to control the solenoid before it moves the flapper to one of its extreme positions, that is, where it closes one of the valve ports. A very fast analog circuit can be used. A microprocessor can be included in the circuit, which has a fast enough processing rate to monitor the position of the valve flapper and move the solenoid so the flapper is maintained in the neutral position. An algorithm can written into the microprocessor so that it can monitor the position of the flapper, practically in real time. The reaction time of the circuit to observe the variation of pressure generated by the valve itself, and regulate the flapper, can be, for example, 200 milliseconds or less, 150 milliseconds or less, 100 milliseconds or less, or 50 milliseconds or less.

The valve systems, circuits, and methods of the present invention can be implemented in any of a variety of devices that comprise a gas valve or air valve, for example, in pneumatically operated systems such as pneumatically operated dialysis machines. Exemplary of the machines in which the valve systems, circuits, and methods of the present invention can be implemented are the dialysis machines described in U.S. Patent Application Publications Nos. US 2011/0196289 A1 and US 2013/0006171 A1, each of which is incorporated herein in its entirety by reference.

The valve system can comprise an electromechanical solenoid that includes an armature and a coil, and a gas valve that includes a magnetic flapper. A power source comprising a power supply can be in electrical communication with the electromechanical solenoid. A controller can be configured to control the power source to supply zero voltage or a first voltage from the power source to the electromechanical solenoid whereby the magnetic flapper is maintained in a first position, for example, where it closes an inlet vacuum port. The controller can also be configured to control the power source to supply a second voltage from the power source to the electromechanical solenoid whereby the flapper is maintained in a second position, for example, where it closes an inlet pressure port. The controller can also be configured to control the power source to supply a third voltage from the power source to the electromechanical solenoid whereby the flapper is maintained in a neutral position between the first position and the second position. The power source can be configured to provide sufficient voltage to the electromechanical solenoid to move the flapper from the second position to the first position, and the valve system can be configured to move the flapper back to the second position when voltage supplied by the power source is discontinued. In some cases, the first position can be a position where the flapper closes an inlet pressure vacuum port and the second position can be where the flapper closes an inlet vacuum port.

The system can include an integrated circuit (IC) and a primary power supply, in electrical communication with the electromechanical solenoid. In some cases, first and second power sources can be used for providing a direct current (DC) power supply and an alternating current (AC) power supply, respectively, to the electromechanical solenoid. A switch can be provided that is in electrical communication with the IC or with the second power source, and also in electrical communication with the electromechanical solenoid. A controller can be used to actuate the switch to change between a cleaning mode position and a normal operation mode position.

When the switch is switched to the cleaning mode position, the switch can cause the IC, or other circuitry, to form a different circuit for controlling the electromechanical solenoid. For example, when two power sources are used, the cleaning mode position can form a circuit that enables power supplied from a second power source to activate the electromechanical solenoid. In some cases, an AC current can thus be applied and used to vibrate the flapper while the flapper is maintained in a neutral position. The vibration can cause particles to be dislodged from the flapper. In the normal operation mode, the switch can be configured to form a different circuit through the IC, or to interrupt the electrical connection from the second power source to the electromechanical solenoid.

The power source can comprise a direct current (DC) power supply, and the controller can be configured to control the power source to supply zero voltage or a first DC voltage from the power source to the electromechanical solenoid to maintain the magnetic flapper in a first position. The controller can also be configured to control the power source to supply a second DC voltage from the power source to the electromechanical solenoid whereby the flapper is maintained in a second position. The controller can also be configured to control the power source to supply a third DC voltage from the power source to the electromechanical solenoid whereby the flapper is maintained in a neutral position between the first position and the second position. The third DC voltage can comprise an average voltage that is greater than zero or the first DC voltage, and less than the second DC voltage. An alternating current (AC) power supply can also be provided and the controller can be configured to supply a DC voltage from the power source to the electromechanical solenoid and simultaneously supply an AC voltage from the AC power supply to the electromechanical solenoid. In so doing, a DC offset to an AC signal can be provided, and the signal, while varying, can be made to not cross a zero point. The varying signal can provide vibrations in the gas valve such that the flapper vibrates and shakes loose particles that might be stuck or otherwise attached to the flapper.

As opposed to a DC power supply, the power source can instead, or additionally, comprise an alternating current (AC) power supply. An integrated circuit can be used to control a singular or primary power supply. The controller can be configured to control the power source to supply zero voltage or a first AC voltage from the power source to the electromechanical solenoid whereby the magnetic flapper is maintained in a first position. The first position can be where, for example, the flapper closes an inlet vacuum port. The controller can also be configured to control the power source to supply a second AC voltage from the power source to the electromechanical solenoid whereby the flapper is maintained in a second position. The second position can be where, for example, the flapper closes an inlet pressure port. The controller can also be configured to control the power source to supply a third AC voltage from the power source to the electromechanical solenoid whereby the flapper is maintained in a neutral position between the first position and the second position.

The valve system can include a housing, and the magnetic flapper can be disposed within the housing. The housing can comprise an inlet pressure port, an inlet vacuum port, and an outlet port. The flapper can be configured to close the inlet pressure port when the flapper is in a first position, and to close the inlet vacuum port when the flapper is in a second position. The power source can be configured to provide sufficient voltage to the electromechanical solenoid to either move the flapper from the first position to the second position, or to move the flapper from the second position to the first position. The default position, where the flapper rests when no activating voltage is supplied to the electromechanical solenoid, can be the first position or the second position.

The valve system can further comprise a pressure sensor in operable communication with the outlet port in the housing. The pressure sensor can be configured to sense the pressure of fluid exiting or entering the outlet port. Circuitry can be provided that is configured to carry a feedback signal, indicative of pressure sensed by the pressure sensor, to the controller. The controller can be configured to control the power source to increase, decrease, or maintain the third voltage, based on the feedback signal, such that the pressure of fluid exiting or entering the outlet port is maintained within an acceptable range of pressures. The acceptable range of pressures can be a range of pressures that correspond to pressures achieved when the flapper is maintained in a neutral position between the first position and the second position.

The valve system can find application in any of a variety of devices and machines. Exemplary pneumatic devices and machines that can use the valve system include pneumatically-operated dialysis machines. Other devices and machines that can benefit from the valve system described herein include air pumps, liquid circulating systems, compressors, liquid feed systems, biocide feed systems for water cooling systems, automated animal feed systems, and the like.

The present invention also includes pneumatically-operated dialysis machines that incorporate a valve system as described herein. The pneumatically-operated dialysis machine can comprise a pressurized fluid source in fluid communication with the inlet pressure port, and a vacuum source in fluid communication with the inlet vacuum port.

A valve system is also included that comprises an electromechanical solenoid having an armature and a coil, a gas valve including a magnetic flapper, a first power source comprising a direct current (DC) power supply in electrical communication with the electromechanical solenoid, and a second power source comprising an alternating current (AC) power supply in electrical communication with the electromechanical solenoid. Alternatively, a primary power source can be used that is controlled by an integrated circuit. The system can include a switch that is in electrical communication with the second power source and the electromechanical solenoid. A controller can be provided that is configured to actuate the switch to change between (1) a cleaning mode whereby the switch forms an electrical connection from the second power source to the electromechanical solenoid, and (2) a normal operation mode whereby the switch interrupts the electrical connection from the second power source to the electromechanical solenoid.

The controller can be configured to (1) supply a first DC voltage from the first power source to the electromechanical solenoid whereby the magnetic flapper is maintained in a first position, (2) supply a second DC voltage from the first power source to the electromechanical solenoid whereby the flapper is maintained in a second position, and (3) supply a third DC voltage from the first power source to the electromechanical solenoid whereby the flapper is maintained in a neutral position between the first position and the second position. The third DC voltage comprises an average voltage that is greater than the first DC voltage and less than the second DC voltage. The first DC voltage can be zero volts and the third DC voltage can be greater than zero volts but less than the second DC voltage. The controller can be configured to simultaneously: (1) supply the third DC voltage from the first power source to the electromechanical solenoid; (2) supply AC voltage from the second power source to the electromechanical solenoid; and (3) control oscillation of the AC voltage to vibrate the flapper while in the neutral position between the first position and the second position, without hitting the first position or the second position. The controller can be configured to supply a DC voltage from the first power source to the electromechanical solenoid and simultaneously supply an AC voltage from the second power source to the electromechanical solenoid. Like in the DC-only embodiment, the valve system can further comprise a housing, wherein the magnetic flapper is disposed within the housing. The housing can comprise an inlet pressure port, an inlet vacuum port, and an outlet port. The flapper can be configured to close the inlet pressure port when the flapper is in the first position, and configured to close the inlet vacuum port when the flapper is in the second position. The first power source can be configured to provide sufficient voltage to the electromechanical solenoid to either move the flapper from the first position to the second position, or to move the flapper from the second position to the first position, depending on the zero voltage default position of the flapper. For example, in some cases, the first power source is configured to provide sufficient voltage to the electromechanical solenoid to move the flapper from the second position to the first position, and the valve system is configured to move the flapper from the first position to the second position when no DC voltage is supplied by the first power source. As with the DC-only embodiment, the valve system can be incorporated in a pneumatically-operated dialysis machine that comprises a pressurized fluid source in fluid communication with the inlet pressure port, and a vacuum source in fluid communication with the inlet vacuum port.

The present invention also provides a method of cleaning a magnetic flapper of a gas valve in a pneumatic system. The method comprises applying a first activating voltage to an electromechanical solenoid of a gas valve. The electromechanical solenoid includes an armature and a coil, and the gas valve includes a magnetic flapper. The first activating voltage that is applied is of sufficient strength to activate the electromechanical solenoid and move the magnetic flapper from a first position, where the magnetic flapper closes a first pneumatic port, to a neutral position, where the magnetic flapper is maintained between the first pneumatic port and a second, different pneumatic port. The electromechanical solenoid can be configured such that, upon application of a second voltage that is greater than the first activating voltage, the magnetic flapper is moved to a second position where it closes the second pneumatic port. The method further involves maintaining the first activating voltage so that the magnetic flapper is held in the neutral position between the first pneumatic port and the second pneumatic port. While being held in the neutral position, gas can be flowed around the magnetic flapper, for example, in a direction from the second pneumatic port to and through the first pneumatic port. Alternatively, alternatingly, or additionally, gas can be flowed around the magnetic flapper in a direction from the first pneumatic port to and through the second pneumatic port. The flow of gas can occur while the magnetic flapper is maintained in the neutral position, to thereby clean the magnetic flapper. The method can also comprise applying an AC voltage to the electromechanical solenoid while the magnetic flapper is maintained in the neutral position. The AC voltage can be made to provide a DC offset to an AC signal and thus vibrate the magnetic flapper. A switch can be provided and the method can entail activating the switch to disconnect the source of the AC voltage and end the cleaning mode. The method can also comprise sensing the pressure of gas entering or exiting a port to the gas valve, and sending a signal indicative of the pressure sensed, to a controller. The first activating voltage can be maintained by using the controller to adjust the first activating voltage, based on the signal, to maintain the magnetic flapper in the neutral position between the first pneumatic port and the second pneumatic port. The method can also comprise first detecting a gas leak in the gas valve before applying the first activating voltage, applying the first activating voltage in response to the detected gas leak, and testing for the gas valve for the leak after the cleaning operation. The cleaning operation can comprise flowing gas around the magnetic flapper, as described herein, to clean the magnetic flapper.

Figure 1A:
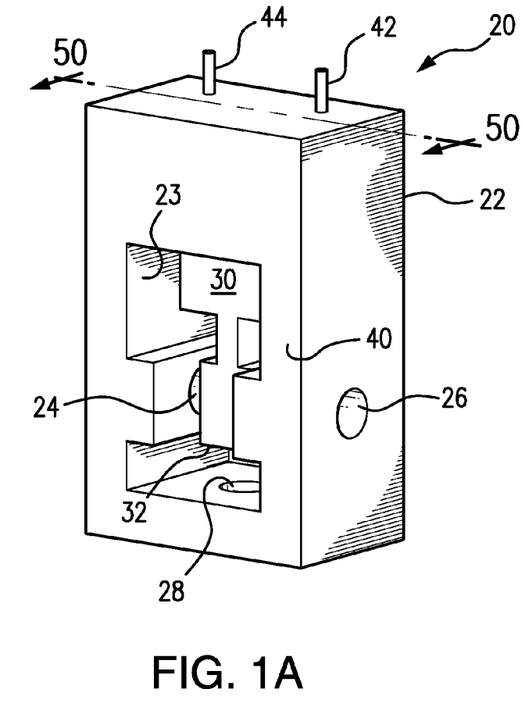
FIG. 1A is a front, right-side perspective view of a flapper valve that can be controlled in accordance with the present invention, showing the flapper in a first position closing an inlet vacuum port while no voltage is applied to a respective solenoid coil.

Referring to the drawings, FIG. 1A shows a front, right-side perspective view of a gas valve or flapper valve 20 that can be used in a valve system in accordance with the present invention and controlled by a method in accordance with the present invention. As shown in FIG. 1A, flapper valve 20 includes a housing 22, having an interior 23, an inlet pressure port 24 that is in fluid communication with interior 23 and with the environment outside of housing 22, an inlet vacuum port 26 that is in fluid communication with interior 23 and with the environment outside of housing 22, and an outlet port 28 that is in fluid communication with interior 23 and with the environment outside of housing 22. In interior 23 of housing 22 is housed a flapper mechanism 30 that includes a flapper 32, a magnet 34 (shown in FIGS. 1B-1D), and a flapper stem 36 between flapper 32 and magnet 34. Flapper 32 and flapper stem 36 can be made of the same material, can be continuous with one another, and can be integrally molded together, for example, of one-piece unitary construction. The material of flapper 32 can comprise an elastomeric material, for example rubber, and the material can also encompass magnet 34 to provide a casing 35 surrounding magnet 34. Although flapper 32 can be flexible, resilient, deformable, and elastomeric, it can move together with magnet 34 such that when magnet 34 is made to move flapper 32 moves with it. Interior 23 can be closed off to the outside environment by attaching a face plate (not shown) to a front surface 40 of housing 22 and to a back surface (not shown) of the housing. Two electrical leads 42 and 44 extend through housing 22, can be connected to leads of a power supply (not shown), and are in electrical communication with a solenoid coil 46 encased in housing 22 and shown in FIGS. 1B-1D. FIG. 1A shows flapper 32 in a first position closing inlet vacuum port 26 while no voltage is applied to solenoid coil 46. A spring or other biasing feature can be used to bias flapper 32 in the position shown, in the absence of an apply voltage. In other cases, the relationship between the coil 46, magnet 34, and the biasing feature can be such that flapper 32 would normally be biased in a position to close inlet pressure port 24 instead of inlet vacuum port 26, in the absence of an applied voltage.

Figure 1B:
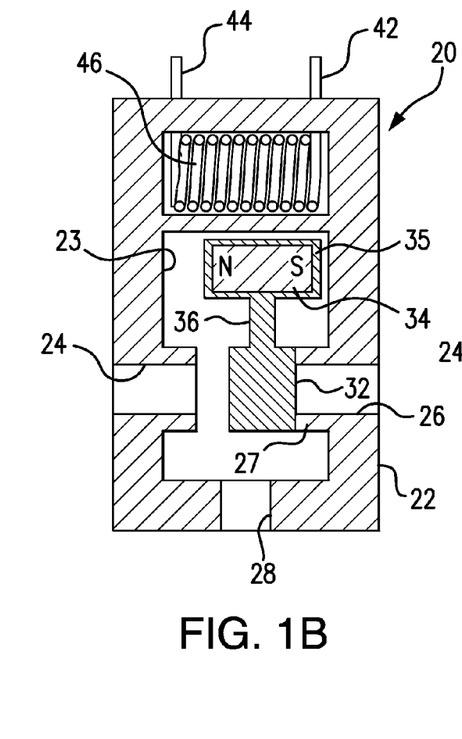
FIG. 1B is a front cross-sectional view of the flapper valve shown in FIG. 1A taken along line 50-50 in FIG. 1A, showing the flapper in the first position closing the inlet vacuum port while no voltage is applied to the solenoid coil.

FIG. 1B is a front cross-sectional view of flapper valve 20 shown in FIG. 1A taken along line 50-50 in FIG. 1A. As can be seen in FIG. 1B, flapper 32 is in a first position, seated firmly against an interior rim 27 of inlet vacuum port 26. In this first position flapper 32 forms a leak-free seal between interior 23 and inlet vacuum port 26. As such, pressurized gas or air forced into interior 23 through inlet pressure port 24 can pass into interior 23 and exit outlet port 28. The pressurized gas or air can be supplied by a source (not shown), for example, a source of clean dry air (CDA). Depending upon what outlet port 28 is connected to, or in fluid communication with, flapper valve 20 can provide a first function when flapper 32 is in this first position.

Figure 1C:
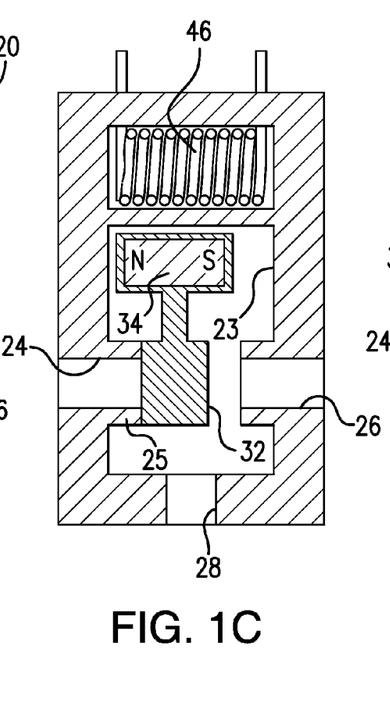
FIG. 1C is a front cross-sectional view of the flapper valve shown in FIG. 1B but wherein the flapper in a second position closing an inlet pressure port while an activating voltage is applied to the solenoid coil.

FIG. 1C is a front cross-sectional view of flapper valve 20 shown in FIG. 1B but wherein flapper 32 is in a second position seated firmly against an interior rim 25 of inlet pressure port 24. Application of an activating voltage to solenoid coil 46 can be used to actuate flapper mechanism 30 and move flapper 32 from the first position shown in FIG. 1B to the second position shown in FIG. 1C. In this second position, flapper 32 forms a leak-free seal between interior 23 and inlet pressure port 24. As such, gas or air drawn can be drawn into outlet port 28, through interior 23, and vacuumed out of interior 23 through inlet vacuum port 26. A source (not shown) of vacuum or relative negative pressure can be in fluid communication with inlet vacuum port 26. Depending upon what outlet port 28 is connected to, or in fluid communication with, flapper valve 20 can provide a second function when flapper 32 is in this second position.

Figure 1D:
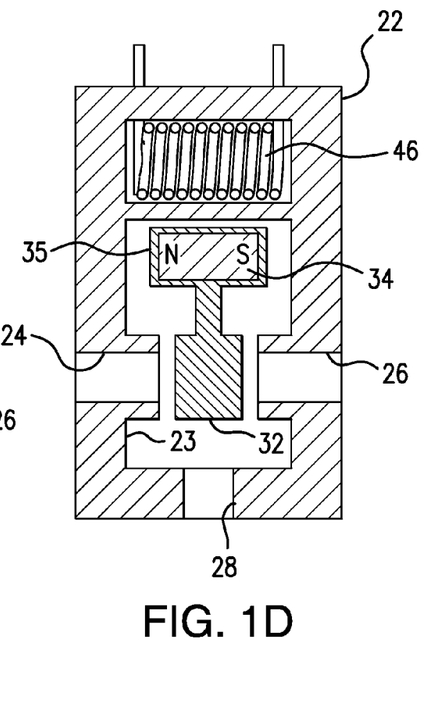
FIG. 1D is a front cross-sectional view of the flapper valve shown in FIGS. 1B and 1C but wherein an intermediate voltage is applied to the solenoid coil and the flapper assumes a neutral position between the inlet vacuum port and the inlet pressure port. Neither port is closed when the flapper is in the neutral position, and air can flow around the flapper to dislodge particles stuck to the flapper.

FIG. 1D is a front cross-sectional view of flapper valve 20 shown in FIGS. 1B and 1C but wherein an intermediate voltage is applied to solenoid coil 46 and flapper 32 assumes a neutral position between inlet pressure port 24 and inlet vacuum port 26. Generally, the intermediate voltage is a voltage that is not as strong as the activating voltage that is applied to solenoid coil 46 to force flapper 32 into the second position shown in FIG. 1C. Neither inlet pressure port 24 nor inlet vacuum port 26 is closed when flapper 32 is in the neutral position shown in FIG. 1D. With flapper 32 in the neutral position shown, air can flow around flapper 32 from inlet pressure port 24, through interior 23, and out inlet vacuum port 26, to thereby dislodge particles stuck to the flapper. By varying the intermediate voltage, for example, by pulse width modulation, by application of alternating current, by varying resistance, or the like, flapper 32 can be made to move toward and away from inlet pressure port 24 and inlet vacuum port 26. The movement toward and away can further assist in dislodging particles stuck to flapper 32.

Figure 2:
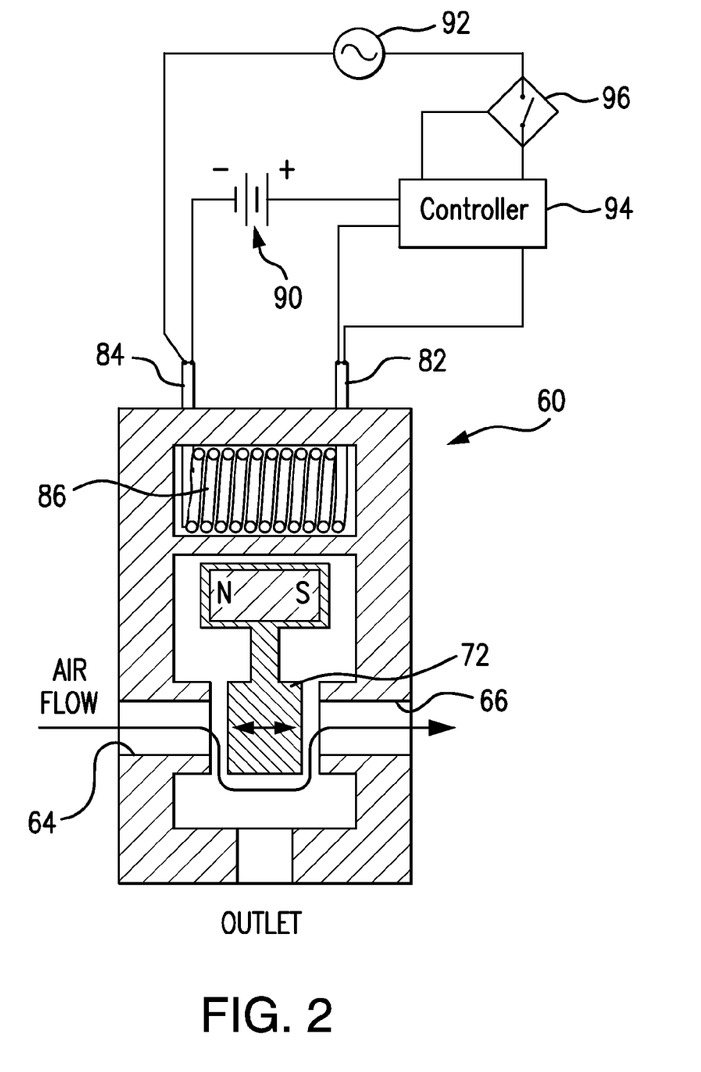
FIG. 2 is a side cross-sectional view of another flapper valve that can be controlled in accordance with the present invention, wherein an intermediate DC voltage is applied to the solenoid coil, the flapper assumes a neutral position between the inlet vacuum port and the inlet pressure port, and an AC voltage is simultaneously applied to the solenoid coil to vibrate the flapper and dislodge particles stuck to the flapper.

FIG. 2 is a side, cross-sectional view of another flapper valve (60) that can be used in a valve system in accordance with the present invention and controlled by a method in accordance with the present invention. As shown in FIG. 2, an intermediate DC voltage can be applied from a DC power supply 90 to a solenoid coil 86 such that a flapper 72 assumes a neutral position between an inlet vacuum port 66 and inlet pressure port 64. A controller 94 is used to regulate the amount of DC voltage supplied to solenoid coil 86 to maintain flapper 72 in the neutral position. While the intermediate DC voltage is being applied to solenoid coil 86 from DC power supply 90, an AC voltage is simultaneously applied from an AC power supply 92 to solenoid coil 86, resulting in vibration of flapper 72 in the neutral position. A switch 96 is provided that is controlled by controller 94 and is in electrical communication with AC power supply 92. Controller 94 is used to regulate the amount of AC voltage supplied to solenoid coil 86 to vibrate flapper 72 in the neutral position without causing the flapper to strike either inlet vacuum port 66 or inlet pressure port 64. The vibration can assist in dislodging particles stuck to flapper 72. As can be seen in FIG. 2, the DC voltage circuit, including DC power supply 90 and controller 94, is in electrical communication with terminals 82 and 84 of solenoid coil 86. The AC voltage circuit, including AC power supply 92 and controller 94, is also in electrical communication with terminals 82 and 84 of solenoid coil 86.

Figure 3:
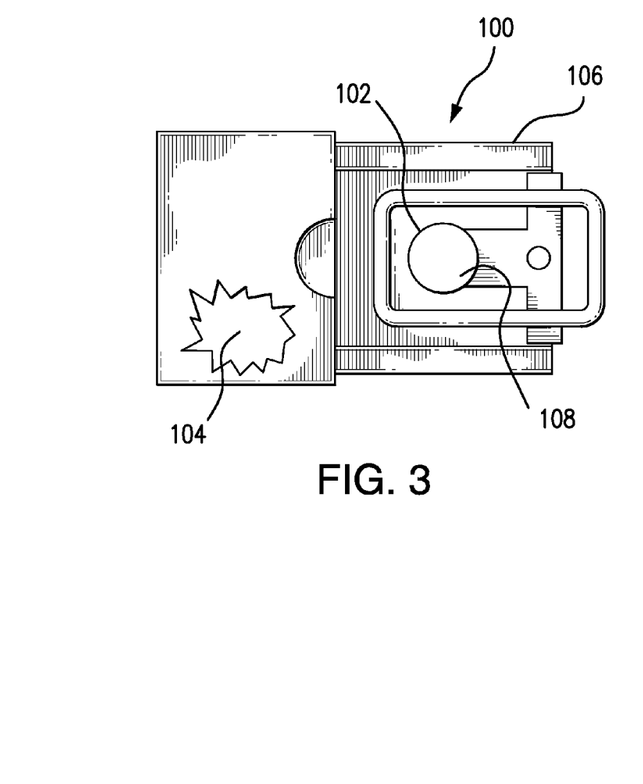
FIG. 3 is a side view of a flapper that can be used in a valve system in accordance with the present invention.

FIG. 3 is a side view of a magnetic flapper 100 that can be used in a valve system in accordance with the present invention. Magnetic flapper 100 comprises an elastomeric flapper 102, a magnet 104, and a casing 106 encompassing magnet 104 and connected to flapper 102. Flapper 102 includes a closure disk 108 that is the portion of flapper 102, which makes contact with an inlet pressure port or an inlet vacuum port of a gas valve.

Figure 4:
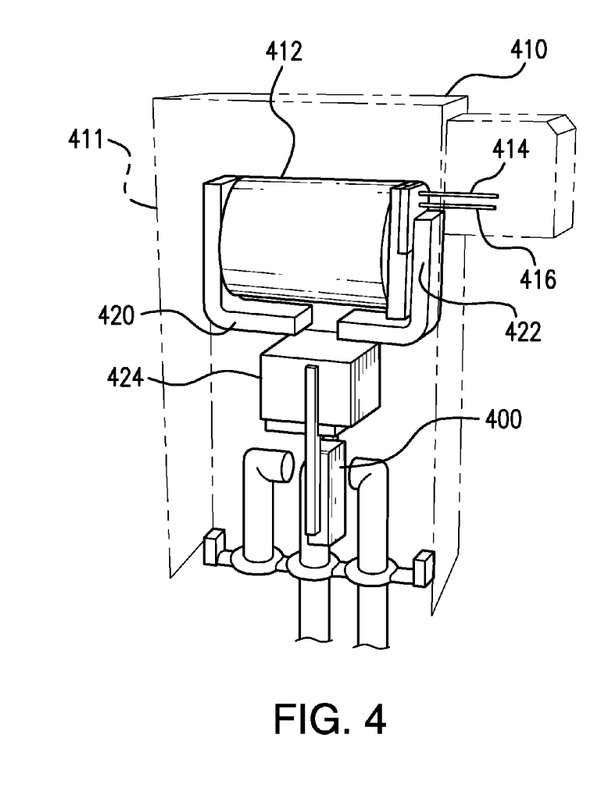
FIG. 4 is a side perspective view of an air valve that incorporates the flapper shown in FIG. 3 and that can be used in a valve system in accordance with the present invention, wherein an outer casing of the air valve has been removed so that the positioning of the flapper can be seen.

FIG. 4 is a front, side perspective view of an air valve 410 that incorporates a magnetic flapper 400, for example, a flapper of the type shown in FIG. 3. Air valve 410 can be used in a valve system in accordance with the present invention. An outer casing 411 of air valve 410 has been removed so that the positioning of magnetic flapper 400 therein can be seen. The coil can be enclosed in a solenoid coil housing 412. Terminals 414 and 416 can be included to connect the solenoid coil to a power source. Pole pieces 420 and 422 can be used to extend the magnetic core and can be considered part of the magnetic core. Pole pieces 420 and 422 can comprise a material of high magnetic permeability and each can serve to direct the magnetic field produced by the magnetic core and carry the magnetic field from the coil to a permanent magnet 424.

Figure 5:
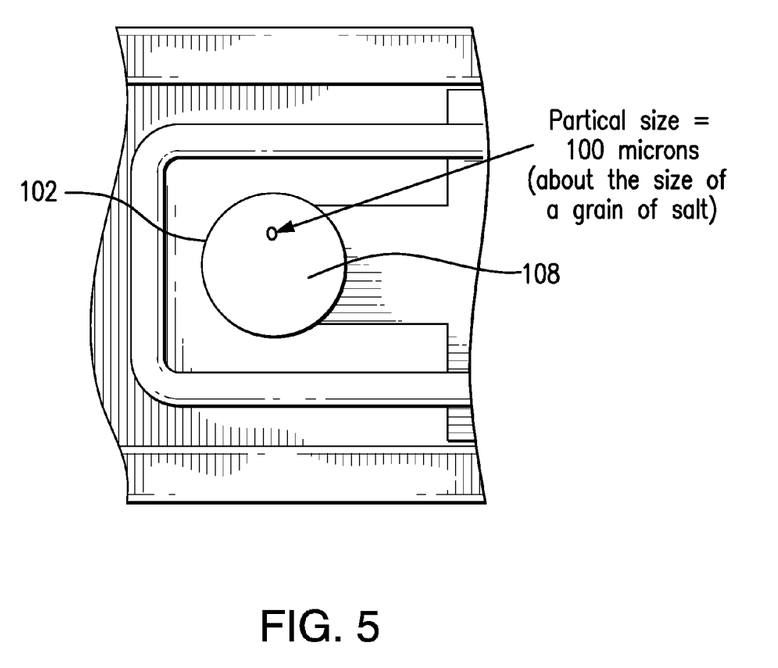
FIG. 5 is an enlarged view of the flapper shown in FIG. 3 and illustrating a foreign particle stuck to the closure disk of the flapper.

FIG. 5 is an enlarged view of flapper 102 shown in FIG. 3 and illustrates a foreign particle stuck to closure disk 108 of flapper 102. The particle shown is about 100 microns across, at its largest dimension, and even at such a small size is large enough to cause an undesirable leak and set-off an alarm system in a pneumatically-operated dialysis machine. According to the present invention, in such a situation, the dialysis machine can detect the leak, undergo a self-cleaning operation to try to fix the leak, and if successful, resume operation of the dialysis machine.

Figure 6:
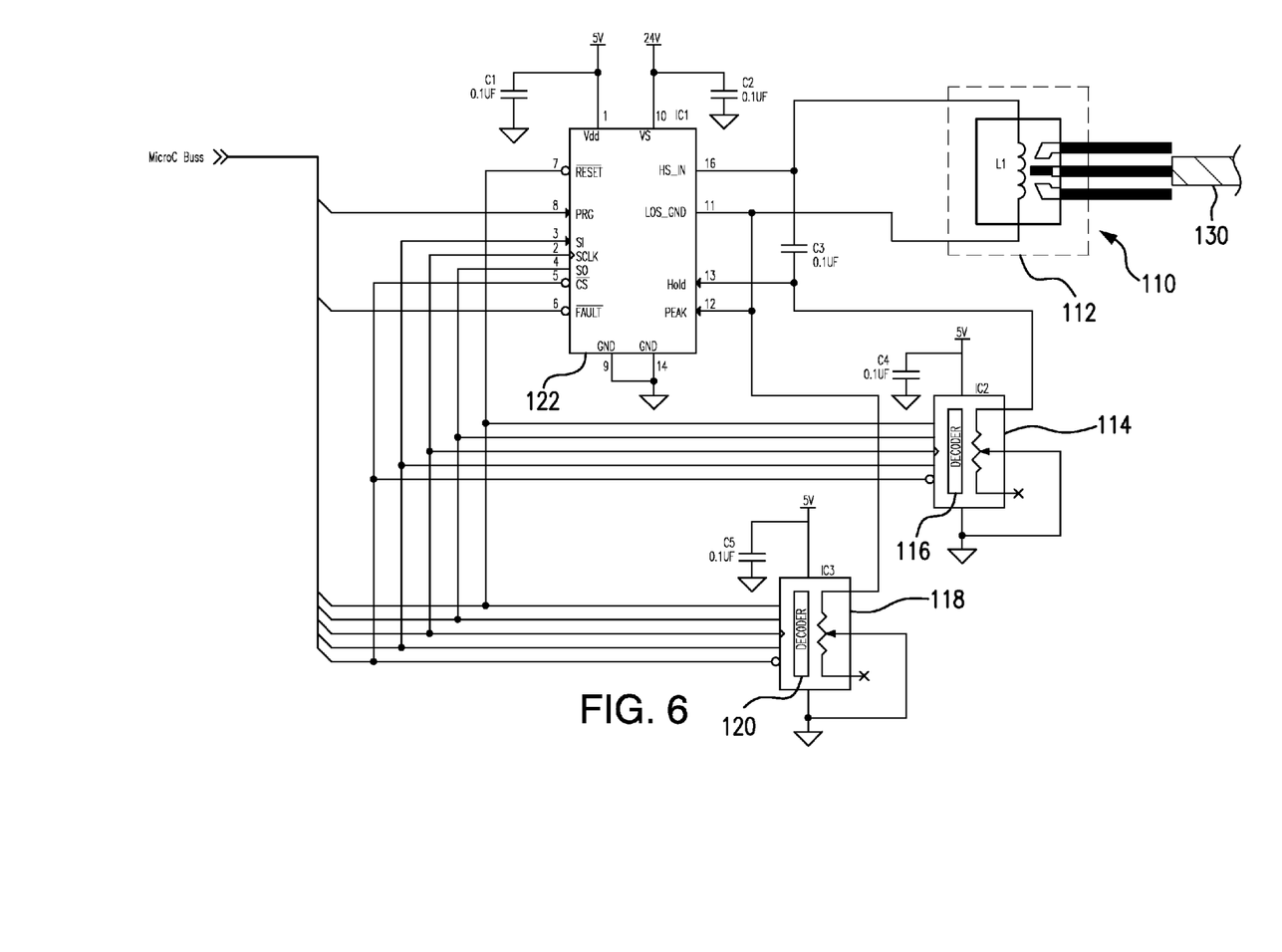
FIG. 6 is a schematic circuit diagram of a microcontroller automated valve driver in accordance with the present invention and which can be used to control a flapper valve to carry out a self-cleaning operation.

FIG. 6 is a schematic circuit diagram of a microcontroller automated valve driver in accordance with the present invention and which can be used to control a flapper valve to carry out a self-cleaning operation. The valve driver can be used in combination with the closed loop system shown in FIG. 7. A shown in FIG. 6, a pneumatic valve device 110 can be provided with a solenoid coil 112 and a pressure outlet tubing 130 that continues in FIG. 7. Pressure outlet tubing 130 leads to a pressure transducer as described in connection with FIG. 7. FIG. 6 also shows a digital potentiometer 114 configured for controlling a hold current duration. Digital potentiometer 114 can be adjusted to vary the length of time that current is supplied to solenoid coil 112 of pneumatic valve device 110. Digital potentiometer 114 includes a decoder 116 configured to receive a serial communication, from a microprocessor, in the form of an ASCII command. Digital potentiometer 114 decodes the serial communication into a resistance value. Digital potentiometer 114 then varies the resistance of its variable resistor based on the decoded serial communication so that current is applied to solenoid coil 112, for an appropriate length of time, to maintain the valve flapper in a neutral position and enable a cleaning operation.

The strength of the current applied to solenoid coil 112, that is, the controlling peak current value, is controlled by a digital potentiometer 118. Digital potentiometer 118 includes a decoder 120 configured similarly to decoder 116. Digital potentiometer 118 is configured to vary the current that is applied to pneumatic valve device 110. As can be seen, digital potentiometers 114 and 118 can be used, together with an integrated circuit, to control the duration and strength of current applied to solenoid coil 112 of pneumatic valve device 110. Digital potentiometers 114 and 118 can be the same as each other, or different from one another.

Digital potentiometers 114 and 118, and pneumatic valve device 110, are parts of microcontroller automated valve driver circuit that further includes a linear integrated circuit 122 also shown in FIG. 6. Linear integrated circuit 122 is configured in electrical communication with digital potentiometers 114 and 118, and with pneumatic valve device 110. Linear integrated circuit 122 can be configured to control a transistor that drives solenoid coil 112. An exemplary device that can be used for linear integrated circuit 122 is part number LM1949 available from Texas Instruments of Dallas, Tex.

The circuit shown in FIG. 6 is configured as a microcontroller automated valve driver that can vary the current peak and current duration applied to pneumatic valve device 110 so that a flapper of the device can be maintained in a neutral position for cleaning. The flapper can be made to vibrate so as to clean the flapper of particles trapped on the flapper, or clean particles lodged near or on a pressure port or vacuum port of the corresponding air valve. The valve driver shown can supply a DC voltage to solenoid coil 112, which balances the pressure and vacuum forces exerted on the flapper of pneumatic valve device 110. When balanced, the flapper can end up in a neutral position, not closing either an inlet pressure port or an inlet vacuum port.

In an exemplary embodiment, one method to determine the appropriate coil DC voltage to achieve such balance is to test the valve in situ. When utilized in, for example, a dialysis machine, testing in situ would entail testing the air valve and circuit after it is installed in the dialysis machine. Outlet pressure from the air valve can be measured from an outlet port of the valve and compared to an applied DC voltage. The DC voltage that enables the valve flapper to be maintained in the neutral position can then be determined.

Figure 7:
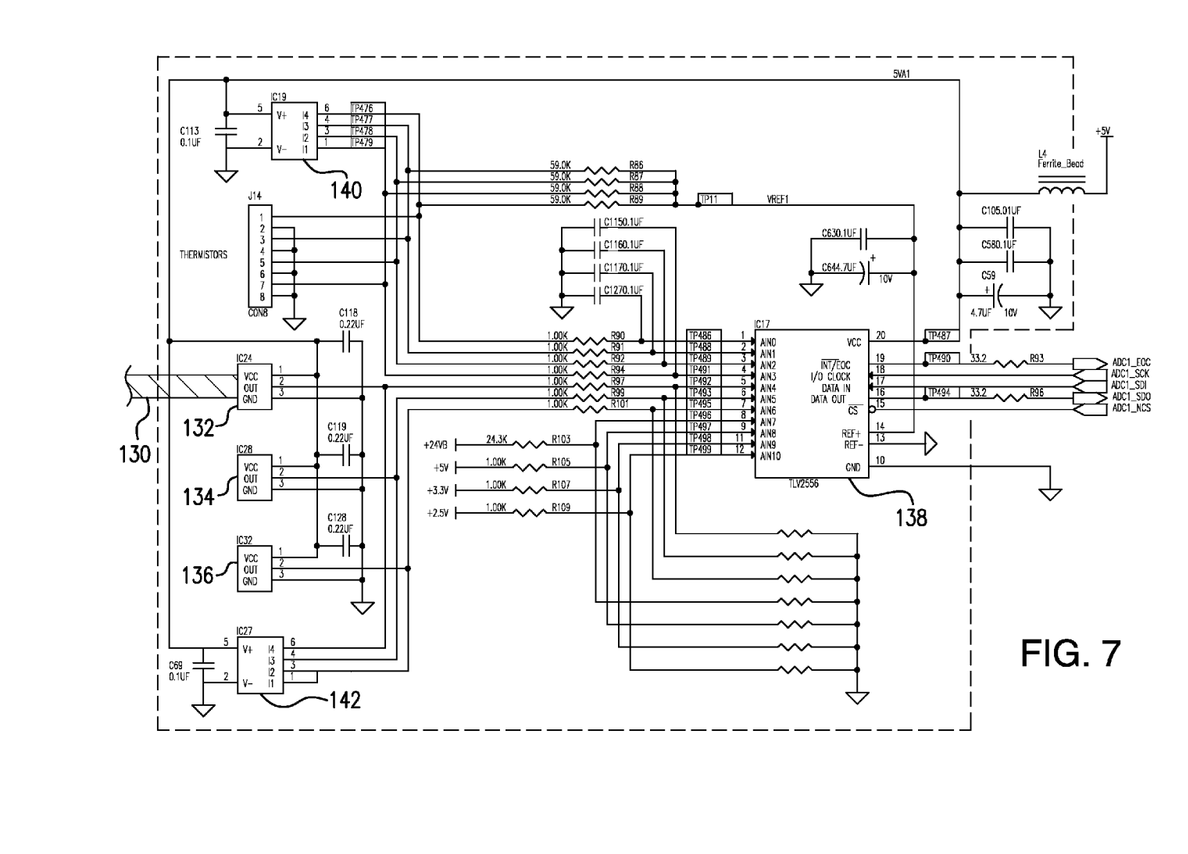
FIG. 7 is a schematic circuit diagram of a closed loop system according to the present invention, which can be used to automatically determine the appropriate intermediate voltage to be applied to the solenoid coil to maintain the flapper in a neutral position. The closed loop system also includes the microcontroller automated valve driver shown in FIG. 6 and uses a signal from a pressure sensor operably connected to the outlet port of the pneumatic valve device shown in FIG. 6, as a feedback signal.

Another method for determining an appropriate DC voltage to be applied to solenoid coil 112 involves the use of a closed loop system built into the dialysis device, which determines an appropriate voltage automatically. Such a closed loop system can use a signal from a pressure sensor on an outlet port of pneumatic valve device 110, as a feedback signal. Using a closed loop system can ensure that appropriate voltage is applied to pneumatic valve device 110 even when pneumatic valve device 110 is exposed to temperature, humidity, and altitude changes. The closed loop system can respond, based on a signal generated from the pressure sensor, and thus change the voltage applied to solenoid coil 112 to maintain the flapper in the neutral position. FIG. 7 shows a schematic diagram of an exemplary closed loop system that can be used for such purpose.

FIG. 7 is a schematic circuit diagram of a closed loop system according to the present invention, which can be used to automatically determine the appropriate intermediate DC voltage to be applied to the solenoid coil to maintain the flapper in a neutral position. The closed loop system also includes the microcontroller automated valve driver shown in FIG. 6 and uses a signal from a pressure sensor on the output port of the pneumatic valve device shown in FIG. 6, as a feedback signal. The circuitry shown in FIG. 7 is in operable communication with the same tubing 130 shown in FIG. 6, and tubing 130 shown in FIG. 7 is a continuation of tubing 130 shown in FIG. 6. Tubing 130 is connected to an outlet port of pneumatic valve device 110 shown in FIG. 6, but the closed loop system could be used to control any air valve.

As can be seen in FIG. 7, tubing 130 is also in operable communication with board-mounted pressure sensors 132, 134, and 136. Pressure sensor 132 can be a board-mounted pressure transducer configured to measure vacuum drawn on tubing 130, for example, vacuum forces of down to −8 pounds per square inch (PSI). Such vacuum forces are generally provided by pneumatically-operated dialysis machines such as the Liberty® Cycler dialysis machine available from Fresenius Medical Care North America of Waltham Mass., in which the present invention can be implemented. An exemplary pressure sensor for such purpose is part number ASDX015D44R available from Honeywell International of Morristown, N.J., which can measure pressures of up to 15 PSI. Tubing 130 can also be an operable communication with pressure sensors 134 and 136, each of which can be configured to measure the maximum pressure generated by the machine in which pneumatic valve device 110 (FIG. 6) is incorporated.

In an example, if pneumatic valve device 110 is incorporated in a pneumatically operated dialysis machine that generates pressures of up to 40 PSI, pressure sensors 134 and 136 should be configured to sense pressures of up to and exceeding 40 PSI. Such pressures are generally provided by pneumatically-operated dialysis machines such as the Liberty® Cycler dialysis machine available from Fresenius Medical Care North America of Waltham Mass. For such an application, each of pressure sensors 134 and 136 can independently be a board-mounted pressured transducer that can measure up to 100 PSI. An exemplary pressure transducer exhibiting such capability is part number ASDX100D44R, available from Honeywell International of Morristown, N.J. Pressure sensors 134 and 136 can be the same as each other, or different from one another.

The closed loop circuit shown in FIG. 7 also depicts a plurality of integrated circuits (IC), capacitors (C), resistors (R), and test points (TP). These designations are also used in the circuitry shown in FIG. 6. Moreover, FIG. 7 also shows a plurality of analog-to-digital converters (ADC), and an 8 pin connector (CON8). The closed loop circuit shown in FIG. 7 also includes a switched-capacitor, analog-to-digital converter 138 that has a plurality of analog inputs (AIN). The inputs are scaled for normal use with 4.096V reference signals. Analog-to-digital converter 138 can be any suitable converter, for example, having 12-bit resolution, 11 channels of analog input, a low power rating, and a sample rate of 200 KSPS. An exemplary analog-to-digital converter that can be used for this purpose is part number TLV2556, available from Texas Instruments of Dallas, Tex.

The exemplary circuit shown in FIG. 7 also includes two diode arrays 140 and 142. Each of diode arrays 140 and 142 can comprise a quad diode array of transient voltage clamping circuits that are designed to suppress electrostatic-discharge (ESD) and other transient over-voltage events. Diode arrays 140 and 142 can be configured to protect input lines to the circuit. An exemplary diode array that can be used for such purpose is part number SP724AHT available from LITTELFUSE, Inc. of Chicago, Ill. Diode arrays 140 and 142 can be the same as each other, or different from one another.

The circuit shown in FIG. 7 also includes a ferrite bead to regulate the current of incoming power and to keep noise off of the 5 volt signal that is supplied to the circuit. The ferrite bead is shown in the upper right-hand portion of FIG. 7.

Using pressure signals generated by the pressure sensors in connection with tube 130, the maximum current can be determined in order to hold pneumatic valve device 110 (FIG. 6) in a neutral, half-opened position for a set amount of time to expose particles and the flapper to a flow of air so that the particles can be blown off of the flapper and blown off of other internal valve mechanisms and ports.

The reaction time of the circuit shown in FIGS. 6 and 7, to observe the variation of pressure generated by the pneumatic valve device 110 and regulate the flapper, can be, for example, 200 milliseconds or less, 150 milliseconds or less, 100 milliseconds or less, or 50 milliseconds or less. It is to be understood that the circuitry shown in FIGS. 6 and 7 is exemplary of a circuit for carrying out such high speed monitoring. The circuitry shown is intended to illustrate, not limit, the present invention.

It is apparent that variations and modifications to the present invention are possible without departing from its scope and spirit. It is therefore to be understood that the appended claims are to be construed as encompassing all features of patentable novelty that reside in the present invention, including all features that would be treated as equivalent thereof by those skilled in the art to which the present invention pertains. All U.S., International, and foreign patents and publications, as well as non-patent literature, referred to herein are hereby incorporated herein by reference in their entireties. All publications, patents, and patent applications mentioned in this specification are herein incorporated by reference to the same extent as if each individual publication, patent, or patent application was specifically and individually indicated to be incorporated by reference.

What is claimed is:

1. A valve system comprising:
a solenoid coil;
a gas valve including a magnetic flapper adjacent to the solenoid coil, the magnetic flapper comprising a flapper and a magnet, the magnet moveable by a magnetic field of the solenoid coil generated when a voltage is applied to the solenoid coil;
a power source comprising a power supply, the power source being in electrical communication with the solenoid coil; and
a controller configured to control the power source to (1) supply zero voltage or a first voltage from the power source to the solenoid coil whereby the magnetic flapper is maintained in a first position, (2) supply a second voltage from the power source to the solenoid coil whereby the flapper is maintained in a second position, and (3) supply a third voltage from the power source to the solenoid coil whereby the flapper is maintained in a neutral position between the first position and the second position.

2. The valve system of claim 1, wherein the power source is configured to provide sufficient voltage to the solenoid coil to move the flapper from the first position to the second position, and the valve system is configured to move the flapper back to the first position when voltage supplied by the power source is discontinued.

3. The valve system of claim 1, wherein the power source comprises a direct current (DC) power supply, and the controller is configured to control the power source to (1) supply zero voltage or a first DC voltage from the power source to the solenoid coil whereby the magnetic flapper is maintained in a first position, (2) supply a second DC voltage from the power source to the solenoid coil whereby the flapper is maintained in a second position, and (3) supply a third DC voltage from the power source to the solenoid coil whereby the flapper is maintained in a neutral position between the first position and the second position.

4. The valve system of claim 3, wherein the third DC voltage comprises an average voltage that is greater than zero or the first DC voltage and less than the second DC voltage.

5. The valve system of claim 3, further comprising an integrated circuit that forms an alternating current (AC) power supply, wherein the controller is configured to supply a DC voltage from the power source to the solenoid coil and simultaneously supply an AC voltage from the AC power supply to the electromechanical solenoid coil.

6. The valve system of claim 1, wherein the power source comprises an alternating current (AC) power supply and the controller is configured to control the power source to (1) supply zero voltage or a first AC voltage from the power source to the solenoid coil whereby the magnetic flapper is maintained in a first position, (2) supply a second AC voltage from the power source to the solenoid coil whereby the flapper is maintained in a second position, and (3) supply a third AC voltage from the power source to the solenoid coil whereby the flapper is maintained in a neutral position between the first position and the second position.

7. The valve system of claim 1, further comprising a housing, wherein the magnetic flapper is disposed within the housing, the housing comprises an inlet pressure port, an inlet vacuum port, and an outlet port, the flapper is configured to close the inlet pressure port when the flapper is in a first position, the flapper is configured to close the inlet vacuum port when the flapper is in a second position, and the power source is configured to provide sufficient voltage to the solenoid coil to either move the flapper from the first position to the second position, or move the flapper from the second position to the first position.

8. The valve system of claim 7, further comprising:
a pressure sensor in operable communication with the outlet port and configured to sense the pressure of fluid exiting or entering the outlet port; and
circuitry configured to carry a feedback signal, indicative of pressure sensed by the pressure sensor, to the controller,
wherein the controller is configured to control the power source to increase, decrease, or maintain the third voltage so that, based on the feedback signal, the pressure of fluid exiting or entering the outlet port is maintained within an acceptable range of pressures.

9. The valve system of claim 8, wherein the acceptable range of pressures is a range of pressures indicative of the flapper being maintained in a neutral position between the first position and the second position.

10. In combination, the valve system of claim 7 and a pneumatically-operated dialysis machine, wherein the pneumatically-operated dialysis machine comprises a pressurized fluid source in fluid communication with the inlet pressure port, and a vacuum source in fluid communication with the inlet vacuum port.

11. A valve system comprising:
a solenoid coil;
a gas valve including a magnetic flapper adjacent to the solenoid coil, the magnetic flapper comprising a flapper and a magnet, the magnet moveable by a magnetic field of the solenoid coil generated when a voltage is applied to the solenoid coil;
a first power source comprising a direct current (DC) power supply, the first power source being in electrical communication with the solenoid coil;
a second power source comprising an alternating current (AC) power supply, the second power source being in electrical communication with the solenoid coil;
a switch in electrical communication with the second power source and the solenoid coil; and
a controller configured to actuate the switch to change between (1) a cleaning mode whereby the switch forms an electrical connection from the second power source to the solenoid coil, and (2) a normal operation mode whereby the switch interrupts the electrical connection from the second power source to the solenoid coil.

12. The valve system of claim 11, wherein the controller is configured to (1) supply a first DC voltage from the first power source to the solenoid coil whereby the magnetic flapper is maintained in a first position, (2) supply a second DC voltage from the first power source to the solenoid coil whereby the flapper is maintained in a second position, and (3) supply a third DC voltage from the first power source to the solenoid coil whereby the flapper is maintained in a neutral position between the first position and the second position.

13. The valve system of claim 12, wherein the third DC voltage comprises an average voltage that is greater than the first DC voltage and less than the second DC voltage.

14. The valve system of claim 12, wherein the first DC voltage is zero volts and the third DC voltage is greater than zero volts but less than the second DC voltage.

15. The valve system of claim 12, wherein the controller is configured to simultaneously: (1) supply the third DC voltage from the first power source to the solenoid coil; (2) supply AC voltage from the second power source to the solenoid coil; and (3) control oscillation of the AC voltage to vibrate the flapper while in the neutral position between the first position and the second position and without hitting the first position or the second position.

16. The valve system of claim 11, wherein the controller is configured to supply a DC voltage from the first power source to the solenoid coil and simultaneously supply an AC voltage from the second power source to the solenoid coil.

17. The valve system of claim 11, further comprising a housing, wherein the magnetic flapper is disposed within the housing, the housing comprises an inlet pressure port, an inlet vacuum port, and an outlet port, the flapper is configured to close the inlet pressure port when the flapper is in a first position, the flapper is configured to close the inlet vacuum port when the flapper is in a second position, and the first power source is configured to provide sufficient voltage to the solenoid coil to either move the flapper from the first position to the second position, or move the flapper from the second position to the first position.

18. The valve system of claim 17, wherein the first power source is configured to provide sufficient voltage to the solenoid coil to move the flapper from the second position to the first position, and the valve system is configured to move the flapper from the first position to the second position when zero DC voltage is supplied by the first power source.

19. In combination, the valve system of claim 17 and a pneumatically-operated dialysis machine, wherein the pneumatically-operated dialysis machine comprises a pressurized fluid source in fluid communication with the inlet pressure port, and a vacuum source in fluid communication with the inlet vacuum port.

20. A method of cleaning a magnetic flapper of a gas valve in a pneumatic system, the method comprising:
    applying a first activating voltage to an solenoid coil of a gas valve, the gas valve comprising a magnetic flapper, the magnetic flapper comprising a flapper and a magnet, the magnet moveable by a magnetic field of the solenoid coil generated when a voltage is applied to the solenoid coil, the first activating voltage being of sufficient strength to activate the solenoid coil and move the magnetic flapper from a first position where the magnetic flapper closes a first pneumatic port, to a neutral position where the magnetic flapper is maintained between the first pneumatic port and a second, different pneumatic port, the solenoid coil being configured such that, upon application of a second voltage that is greater than the first activating voltage, the magnetic flapper is moved to a second position where it closes the second pneumatic port;
    maintaining the first activating voltage so as to maintain the magnetic flapper in the neutral position between the first pneumatic port and the second pneumatic port; and
    flowing a gas around the magnetic flapper from the second pneumatic port to the first pneumatic port, while the magnetic flapper is maintained in the neutral position, to thereby clean the magnetic flapper.

21. The method of claim 20, further comprising applying an alternating current (AC) voltage to the solenoid coil while the magnetic flapper is maintained in the neutral position, to vibrate the magnetic flapper.

22. The method of claim 21, further comprising activating a switch to disconnect a source of the AC voltage and end a cleaning mode.

23. The method of claim 21, further comprising:
    sensing the pressure of gas entering or exiting a port to the gas valve; and
    sending a signal indicative of the pressure sensed, to a controller,
    wherein the maintaining the first activating voltage comprises using the controller to adjust the first activating voltage, based on the signal, to maintain the magnetic flapper in the neutral position between the first pneumatic port and the second pneumatic port.

24. The method of claim 21, further comprising:
    detecting a gas leak in the gas valve before applying the first activating voltage;
    applying the first activating voltage in response to detecting the gas leak; and
    testing for a gas leak in the gas valve after flowing the gas around the magnetic flapper to clean the magnetic flapper.

* * * * *